US00PP16388P2

(12) United States Plant Patent
Zary

(10) Patent No.: US PP16,388 P2
(45) Date of Patent: Mar. 28, 2006

(54) HYBRID TEA ROSE PLANT NAMED 'JACZEMAN'

(50) Latin Name: *Rosa hybrida*
Varietal Denomination: JACzeman

(75) Inventor: Keith W. Zary, Somis, CA (US)

(73) Assignee: Jackson and Perkins Wholesale, Inc., Medford, OR (US)

( * ) Notice: Subject to any disclaimer, the term of this patent is extended or adjusted under 35 U.S.C. 154(b) by 76 days.

(21) Appl. No.: 10/848,709

(22) Filed: May 18, 2004

(51) Int. Cl.
*A01H 5/00* (2006.01)

(52) U.S. Cl. ..... Plt./132

(58) Field of Classification Search ..... Plt./132, Plt./134, 135, 130, 145
See application file for complete search history.

*Primary Examiner*—Anne Marie Grunberg
*Assistant Examiner*—June Hwu
(74) *Attorney, Agent, or Firm*—Klarquist Sparkman LLP

(57) ABSTRACT

Hybrid tea rose plant having long flower life both on the plant and in the vase; thick petal substance; bright yellow tipped with orange flower color; and spicy fragrance.

1 Drawing Sheet

Genus and species: *Rosa hybrida.*
Variety denomination: 'JACzeman'.

ORIGIN OF THE INVENTION

The present invention relates to a new and distinct variety of a hybrid tea rose plant named 'JACzeman' which was originated by me by crossing an unnamed, unpatented seedling (seedling×seedling), with the unpatented variety 'AROgoru' (Baron G. de l'ain×unknown).

BACKGROUND OF THE INVENTION

The primary objective of this breeding was to produce a new rose variety having the tall upright plant and yellow and orange flower color of the female parent combined with the long flower life and large bloom production of the male plant.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Long flower life both on the plant and in the vase.
2. Thick petal substance.
3. Bright yellow tipped with orange flower color.
4. Spicy fragrance.

Asexual reproduction of this new variety by budding, as performed at Wasco and Somis, Calif., shows that the foregoing and all other characteristics and distinctions come true to form and are established and transmitted through succeeding propagations.

COMPARISON WITH PARENTS

In the subject variety the female parent is a tall yellow, orange and pink blend hybrid tea, and the male parent 'AROgoru' is a light pink hybrid tea. JACzeman has no pink in its blooms.

COMPARISON WITH SIMILAR VARIETY

The closest varieties are 'AROyqueli' (U.S. Plant Pat. No. *5177*) (Gold Medal) and its sport 'STARqueli' (U.S. Plant Pat. No. 8861) (Magic Lantern). 'JACzeman' differs from these two varities in having a deeper yellow color, smaller open blooms and lasts on the plant and in the vase for 3–5 days longer.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:
*Seed parent.*—Unnamed seedling.
*Pollen parent.*—'AROgoru'.

FLOWER

Observations made from plants commencing at two years of age grown in a garden environment at Somis and Wasco, Calif.

Blooming habit: Continuous.
Bud:
*Size.*—About 30–35 mm long and 18–20 mm in diameter when the petals start to unfurl.
*Form.*—The bud form is long, pointed ovoid.
*Color.*—When sepals first divide, bud color is Yellow-Orange Group 15B edged in Red Group 40C. When half blown, the upper sides of the petals are Yellow-Orange Group 15B with Red Group 40C along margin; and the lower sides of the petals are Yellow-Orange Group 15C with Red Group 40C along margin.

*Sepals.*—Color: Upper surface: Yellow-Green Group 146C with Yellow-Green Group 145C at base. Lower surface: Yellow-Green Group 144A. Length: 40–50 mm. Width: 10–14 mm. Shape: Subulate. Surface texture: Upper surface: Hoary. Lower surface: Smooth. There are three heavily appendaged sepals. There are two unappendaged sepals with glandular and ciliolate edges.

*Receptacle.*—Color: Yellow-Green Group 144B. Shape: Funnel. Size: Small, about 6–8 mm long× 8–10 mm wide. Surface: Smooth.

*Peduncle.*—Length: Long, averaging about 14–20 cm. Surface: Smooth. Color: Yellow-Green Group 144B. Strength: Stiff, erect.

Bloom:

*Size.*—Medium. Average open diameter is about 9–11 cm.

*Borne.*—Singly and in pyramidal clusters of 3–5 blooms.

*Stems.*—Strength: Strong. Average length is about 36–40 cm with a diameter of 5–8 mm. Color: Yellow-Green Group 146B.

*Form.*—When first open: High centered. Permanence: Outer petal edges curl slightly.

*Petalage.*—Number of petals under normal conditions: 25.

*Color.*—The upper sides of the petals are Yellow-Orange Group 15B edged in Red Group 40C. The reverse sides of the petals are Yellow-Orange Group 15B edged in Red Group 40C. The base of each petal has Yellow Group 12A. The major color on the upper side is Yellow-Orange Group 15B.

*Variegations.*—None.

*Discoloration.*—The general tonality at the end of the first day: Yellow-Orange Group 15B. At the end of the third day: Yellow-Orange Group 15B. Further aging: Fades to Yellow-Orange Group 15D and at day five petals drop.

*Fragrance.*—Moderate, spicy.

Petals:

*Texture.*—Thick, coriaceous.

*Shape.*—Obovate.

*Surface.*—Smooth.

*Margin.*—Entire. Apex Shape: Mucronate. Base Shape: Cuneate.

*Form.*—Tips slightly recurved.

*Arrangement.*—Imbricated.

*Petaloids.*—Number: 0–3. Color: Yellow-Orange Group 15B edged in Red Group 40C. Length: 2–9 mm. Width: 1–4 mm.

*Persistence.*—Petals drop off cleanly before drying.

*Lastingness.*—On the plant: Long (about 7–9 days). As a cut flower: Long (about 9–11 days).

Reproductive parts:

*Stamens.*—Number: 90–100. Length: 10–12 mm. Anthers: Length: 3–4 mm. Color: Yellow-Orange Group 16B. Arrangement: Regular around styles. Filaments: Color: Yellow Group 13C. Length: 6–9 mm. Pollen: Color: Greyed-Orange Group 167D.

*Pistils.*—Number: 120–140. Length: 9–11 mm. Styles: Color: Bottom half is Yellow Group 2D, top half is Greyed-Purple Group 184A. Length: 8–10 cm. Stigmas: Color: Greyed-Orange Group N 167C. Length: 1 mm.

*Hips.*—None observed.

PLANT

*Form.*—Bush.

*Growth.*—Virorous, upright, branching.

*Age at maturity.*—Two years.

*Mature plant.*—Height: 140–160 cm. Width: 100–120 cm.

*Rootstock.*—Dr. Huey.

Foliage: Number of leaflets on normal mid-stem leaves: 5–7.

*Size.*—Large. About 14–18 cm long×10–12 cm wide.

*Quantity.*—Normal.

*Color.*—New foliage: Upper side: Greyed-Purple Group 185A. Lower side: Greyed-Purple Group N186D. Old foliage: Upper side: Yellow-Green Group 147A. Lower side: Yellow-Green Group 148B.

Leaflets:

*Size.*—About 4–6 cm long×3–4 cm wide.

*Shape.*—Broadly oval.

*Base shape.*—Rounded.

*Apex shape.*—Cuspidate.

*Texture.*—Coriaceous and lustrous.

*Edge.*—Serrated.

*Serrations.*—Single, small.

*Petiole.*—Color: Yellow-Green Group 144B. Length: 16–20 mm. Surface Texture: Smooth, with an occasional prickle.

*Petiole rachis.*—Color: Yellow-Green Group 144B. Underside: Prickles.

*Auricle shape, if present.*—None.

*Stipules.*—Length: 18–20 mm glandular. Color: Upper surface: Yellow-Green Group 147A. Lower surface: Yellow-Green Group 148B.

*Disease resistance.*—Resistant to rust and susceptible to powdery mildew and blackspot under normal growing conditions.

*Pest persistence.*—N/A.

*Vein color.*—Yellow-Green Group 144B.

*Venation pattern.*—Reticulate.

Wood:

*New wood.*—Color: Greyed-Red Group 178B. Bark: Smooth.

*Old wood.*—Color: Yellow-Green Group 146B. Bark: Smooth.

Prickles:

*Quantity.*—On main canes from base: None. On laterals from main canes: Few (2–3 per 10 cm of stem).

*Form.*—Straight.

*Length.*—8–10 mm.

*Color when young.*—Red Group 47A.

*Color when mature.*—Greyed-Yellow Group 160D.

Small prickles:

*Quantity.*—On main stalks: None. On laterals: None.

Winter hardiness: Hardy to Zone 5.

I claim:

1. A new and distinct variety of rose plant of the hybrid tea class, substantially as herein shown and described, characterized particularly by long flower life both on the plant and in the vase; thick petal substance; bright yellow tipped with orange flower color; and spicy fragrance.

* * * * *

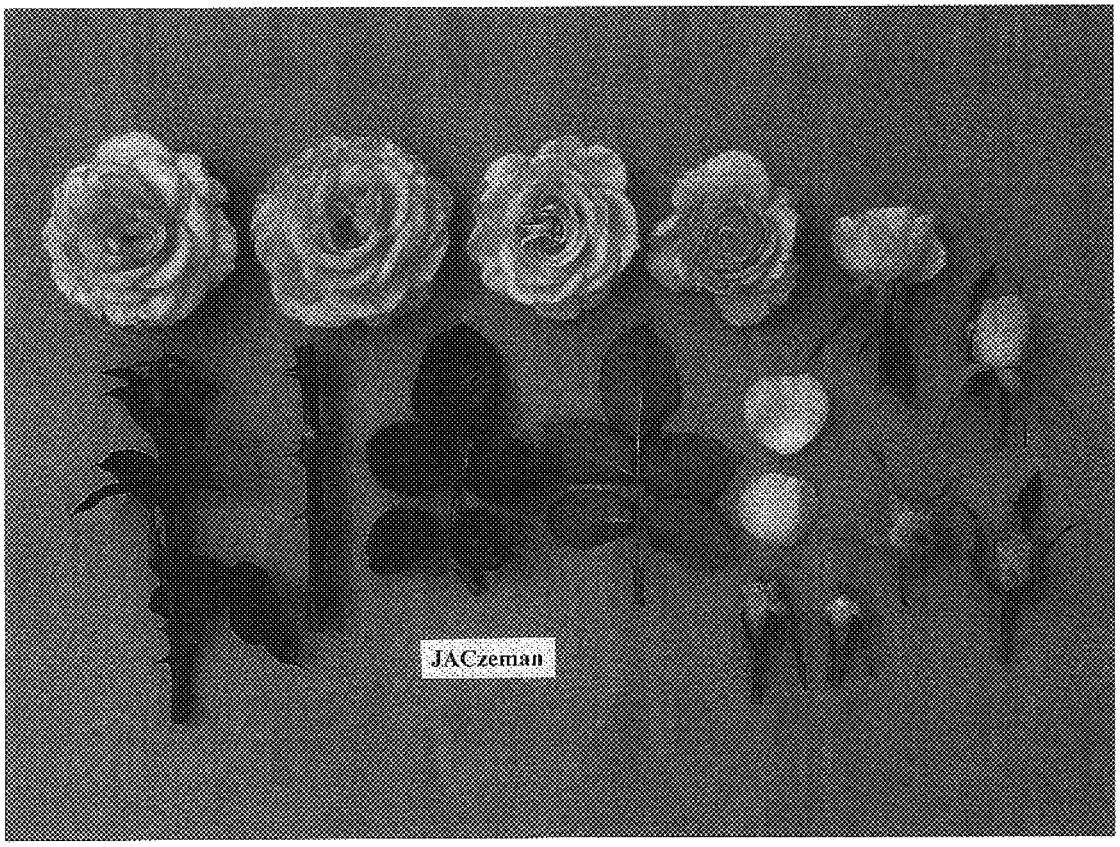
JACzeman